United States Patent [19]

Steltenkamp et al.

[11] Patent Number: 4,547,361

[45] Date of Patent: Oct. 15, 1985

[54] STABILIZING OF CINNAMIC ALDEHYDE-CONTAINING FLAVORS WITH PROPYLENE GLYCOL AND DIPROPYLENE GLYCOL

[75] Inventors: Robert J. Steltenkamp, Somerset; Miriam L. Douglass; Gerard E. Natarelli, both of Piscataway, all of N.J.

[73] Assignee: Colgate-Palmolive Company, New York, N.Y.

[21] Appl. No.: 578,942

[22] Filed: Feb. 10, 1984

[51] Int. Cl.⁴ ............................ A61K 7/16; A61K 7/26
[52] U.S. Cl. ........................................ 424/49; 424/58
[58] Field of Search ................................... 424/49-58

[56] References Cited

U.S. PATENT DOCUMENTS

| | | | |
|---|---|---|---|
| 2,184,526 | 12/1939 | Meuly | 167/94 |
| 3,864,472 | 2/1975 | Pensak et al. | 425/54 |
| 3,867,557 | 2/1975 | Neely et al. | 426/175 |
| 3,928,560 | 12/1975 | Neely et al. | 424/52 |
| 3,957,964 | 5/1976 | Grimm | 424/10 |
| 3,988,432 | 10/1976 | Steltenkamp et al. | 424/49 |
| 4,001,438 | 1/1977 | Marmo et al. | 426/96 |
| 4,132,771 | 1/1979 | Schreiber et al. | 424/52 |
| 4,187,287 | 2/1980 | Schreiber et al. | 424/49 |
| 4,242,323 | 12/1980 | Vlock | 424/58 |
| 4,431,631 | 2/1984 | Clipper et al. | 424/53 |

*Primary Examiner*—Shep K. Rose
*Attorney, Agent, or Firm*—Robert L. Stone; Murray M. Grill; Herbert S. Sylvester

[57] ABSTRACT

Dentifrice formulations having improved stability against discoloration upon aging comprising an unsaturated aldehyde flavoring agent selected from the group consisting of cinnamic aldehyde and citral and an effective amount in excess of 5% and preferably about 10–45% of a color stabilizer selected from the group consisting of propylene glycol, dipropylene glycol and mixtures thereof, in a dental vehicle free of oxidizing agents such as peracids and salts thereof and maintained at a pH below 8.5 and preferably acid to slightly alkaline (about 5–7.5).

17 Claims, 1 Drawing Figure

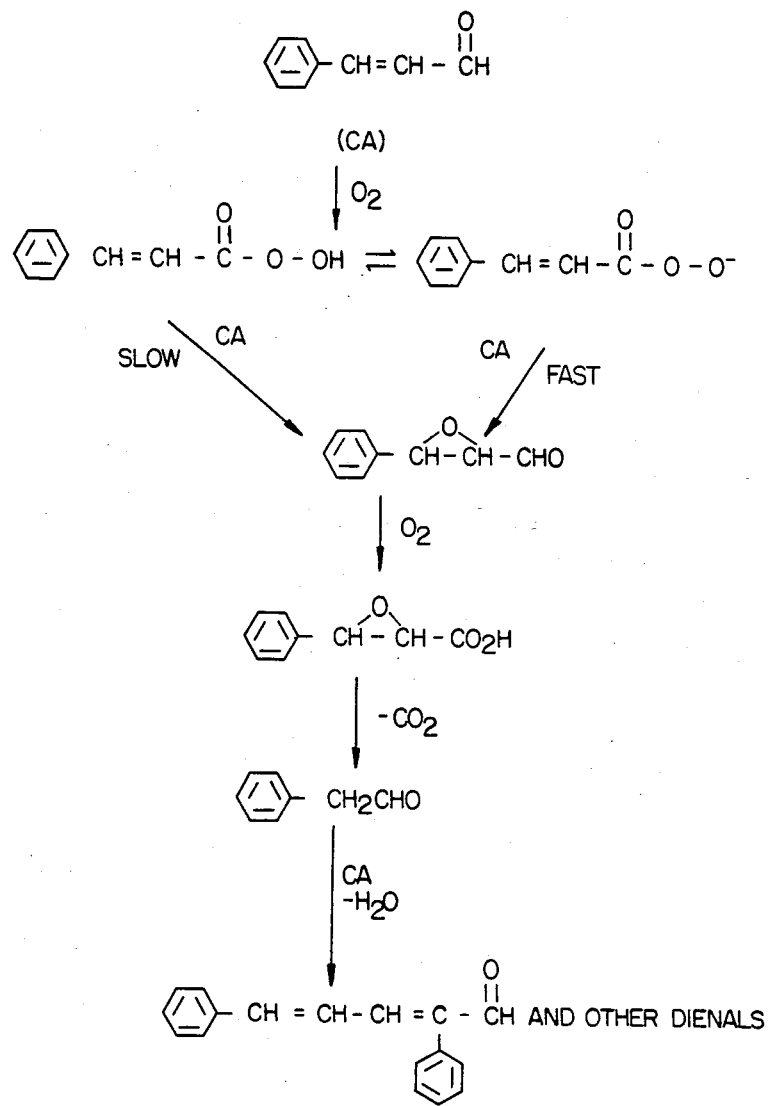
AUTOXIDATION OF CINNAMIC ALDEHYE

STABILIZING OF CINNAMIC ALDEHYDE-CONTAINING FLAVORS WITH PROPYLENE GLYCOL AND DIPROPYLENE GLYCOL

BACKGROUND OF THE INVENTION

This invention relates to a color-stabilized dentifrice composition comprising a cinnamic aldehyde or citral flavorant which is subject to discoloration/yellowing upon aging, and propylene glycol and/or dipropylene glycol which significantly reduces and/or prevents discoloration, and maintaining the pH of said composition below 8.5 and preferably at a slightly alkaline to acid pH. The dentifrice vehicle may be aqueous or anhydrous.

The prior art is replete with dental formulations comprising the combination of a cinnamic aldehyde or citral flavorant and propylene glycol or dipropylene glycol as shown in U.S. Pat. Nos. 3,867,557 and 3,928,560 wherein oral compositions containing 0.0001-20% paramethoxycinnamaldehyde flavoring agent is dissolved in 100 parts propylene glycol; U.S. Pat. No. 4,132,771 and U.S. Pat. No. 4,187,287, wherein a two-tone flavored dentifrice containing cinnamon flavor is in a propylene glycol vehicle; U.S. Pat. No. 4,242,323 wherein a plaque inhibiting oral composition containing cinnamon oil flavorant also utilizes propylene glycol as the liquid vehicle; and U.S. Pat. No. 3,864,472 relating to a clear lemon-flavored mouthwash containing lemon oil, cinnamic aldehyde and glycerine or propylene glycol. U.S. Pat. No. 4,001,438 also discloses flavor formulations comprising citral and/or cinnamic aldehyde as a component in a physically entrapped flavor composition which is admixed with a non-confined flavor oil, a suspending agent and preferably a small amount (0.5%) of propylene glycol which improves product stability (column 6 lines 32-33), useful in oral compositions. However, there is no recognition in this group of patents of the discoloration or yellowing problem due to aging associated with the use of the cinnamic aldehyde flavorant. These patents relate to different aspects in dentifrice formulations. The disclosure of the combination of cinnamic aldehyde flavorant and propylene glycol is incidental to a general discussion of flavorants and typical humectants.

The prior art also recognizes the fading and/or deterioration of flavors as shown in U.S. Pat. No. 3,957,964 wherein the flavoring material, which includes oil of cinnamon or orange, is encapsulated and kept separate from the dentifrice base (which may include propylene glycol) during storage until released when the dentifrice is used, thereby providing a more stable and fresher tasting flavored dentifrice. However, there is no mention in aforesaid patent of the stabilization of the cinnamic aldehyde or citral flavor with propylene glycol or dipropylene glycol.

U.S. Pat. No. 2,184,526 also recognizes the instability against oxidation by air of p-isopropyl-α-methylhydrocinnamic aldehyde as a perfume ingredient, wherein the aldehyde is converted into the corresponding acid, thereby destroying the aldehyde odor. The addition of alcohols of the aromatic or terpene series stabilizes the aldehyde against air oxidation, by converting the aldehyde into a hemi-acetal of said alcohol, said hemi-acetal functioning as the perfume material.

None of the above cited art discloses the use of propylene glycol or dipropylene glycol in excess of 5% by weight, in a dentifrice, free of oxidizing agents and maintained at an acid or neutral pH, containing the cinnamic aldehyde or citral flavor, to reduce discoloration of said flavorant upon aging.

SUMMARY OF THE INVENTION

It has been unexpectedly found that the discoloration on aging of dentifrice products that are flavored with cinnamic aldehyde or citral can be reduced and/or prevented by the addition of propylene glycol or dipropylene glycol in excess of 5% by weight and preferably about 10-45% by weight. It is essential that the dental vehicle be free of oxidizing agents and be maintained at an acid to neutral pH for said propylene glycol or dipropylene glycol to function effectively.

Accordingly, the primary object of this invention is to provide dentifrice formulations containing cinnamic aldehyde or citral flavor that does not turn yellow or discolor with age.

Another object of this invention is to provide a color stabilized dental cream or mouthwash comprising cinnamic aldehyde or citral flavor and an effective amount of a color stabilizer selected from the group consisting of propylene glycol and dipropylene glycol and mixtures thereof.

Still another object of this invention is to provide a color stabilized cinnamic aldehyde- or citral-containing aqueous or anhydrous dentifrice maintained at a pH below 8.5, and preferably at a neutral to acid pH.

Another object of this invention is to provide an acid or neutral color stabilized aldehyde flavorant-containing dentifrice free of oxidizing agents.

Still another object of this invention is to provide a color stabilized white dental cream or mouthrinse containing cinnamic aldehyde or citral flavorant.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel dentifrice of this invention, which has improved stability against discoloration upon aging, comprises an unsaturated aldehyde-containing flavorant selected from the group consisting of cinnamic aldehyde and citral which is subject to discoloration upon aging, and an effective amount in excess of 5% by weight of a color stabilizer selected from the group consisting of propylene glycol and dipropylene glycol, in an aqueous or anhydrous dental vehicle free of oxidizing agents and maintained at a pH below 8.5, and preferably at an acid to slightly alkaline pH of about 5-7.5.

More specifically, this invention relates to a color stabilized white dental cream or mouthwash, free of oxidizing agents and having an acid to neutral pH comprising about 0.1-1% by weight of cinnamic aldehyde or citral flavorant and about 10-45% propylene glycol or dipropylene glycol.

It has been found that the cinnamic aldehyde or citral flavorant decomposed upon aging to form conjugated unsaturated aldehydes (dienals). These dienals are responsible for the yellowing or discoloration evident with cinnamic aldehyde or citral in white dental products which include liquids or creams (pastes).

Commercial dental creams utilizing low levels of cinnamic aldehyde have circumvented the discoloration problem by coloring the product, e.g., red, blue, light green, etc. However, in white dental cream, the discoloration from a low level of cinnamic aldehyde is unacceptable.

The autoxidation of cinnamic aldehyde (CA) proceeds according to the following mechanism:

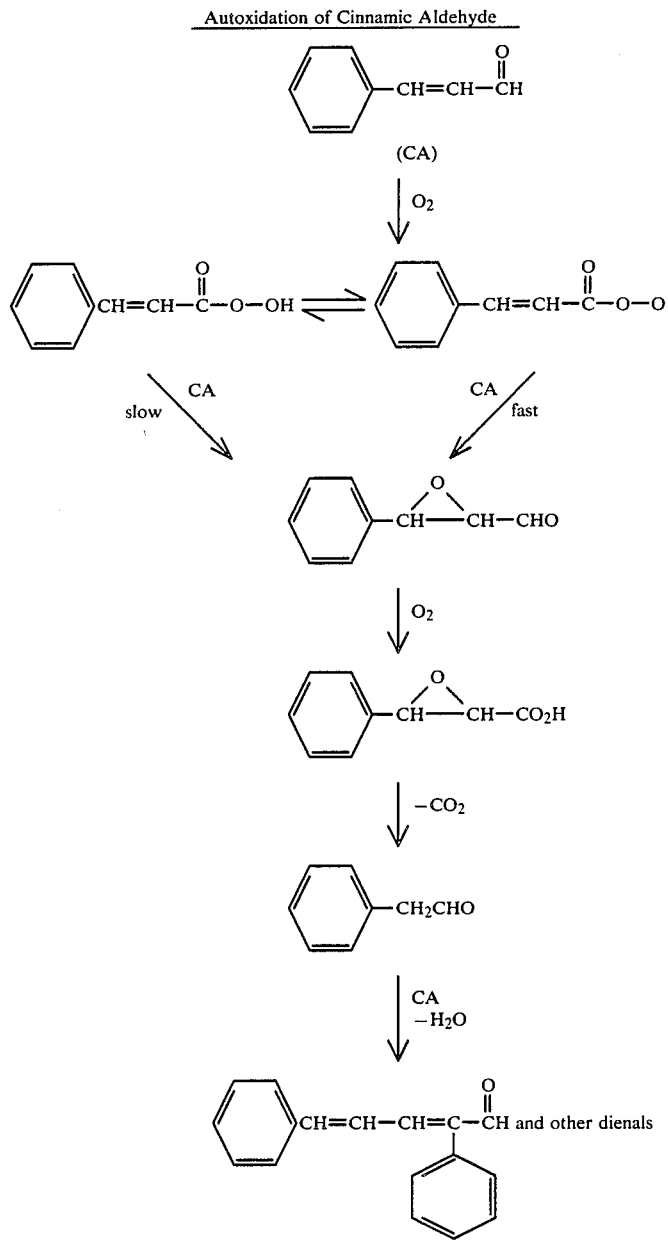

The acid forms even when samples are stored in tightly capped bottles with the head space flushed with nitrogen. Cinnamaldehyde is quite sensitive to small amounts of oxygen. Since cinnamic acid is white, its formation, which occurs within a short time after exposure, is not responsible for the yellowing of cinnamaldehyde. The intensity of the yellow color increases with time of oxygen exposure, rather than with the quantity of oxygen, indicating that more complex oxidation occurs during aging. Specifically, the formation of conjugated dienals are the intensive yellow components responsible for the discoloration and yellowing of the cinnamic aldehyde.

It has now been found that discoloration from low levels of cinnamic aldehyde (a maximum of about 1% by weight) is reduced in the presence of propylene glycol and/or dipropylene glycol. These materials in a 1:1 weight ratio with cinnamic aldehyde are effective in preventing nearly all yellowing on aging in glass. However, in dental cream at levels of 1–5% they showed only slight reduction of yellowing from 1% cinnamic aldehyde. Since these glycols are odorless, it is practical to incorporate them in much higher amounts. The substitution of water or of glycerine in dental formulations by propylene glycol or dipropylene glycol is effective in preventing the yellowing of flavors containing cinnamic aldehyde or citral. When a non-aqueous paste is formulated by replacing the water with either glycol, no discoloration is observed. Also, the replacement of the 22% glycerine in a dental cream by propylene glycol significantly reduced yellowing.

The mechanism of the glycol effect is believed to involve acetal and hemi-acetal formation/complexation. The glycols are believed to be effective by complexing the aldehydes through acetal formation. Since aldehydes are involved in four different phases of the dienal formation mechanism (FIG. I), reaction with glycol would significantly interfere with dienal generation. Analysis of the aged 1:1 CA/propylene glycol sample showed appreciable acetal formation with some hemi-acetal. This reversible reaction does have the problem of consuming some of the cinnamic aldehyde. In practice, the cinnamic aldehyde may have to be increased to compensate for this loss.

The autoxidation of cinnamic aldehyde is inhibited (interrupted) by the presence of the propylene glycol due to the formation of glycol acetals which form rapidly at room temperature, and increase with time. This prevents the formation of the dienals which are responsible for the yellowing upon aging.

This means for reducing discoloration of cinnamic aldehyde is also applicable to other conjugated unsaturated aldehydes such as citral, $(CH_3)_2C=CHCH_2CH_2C(CH_3)=CHCHO$. Citral is another flavor commonly used in dentifrice compositions.

Yellowing of a liquid mixture of cinnamic aldehyde with propylene glycol or dipropylene glycol was measured on the Gardner tintometer, both when freshly prepared and after aging for 24 hours in a vial at 90° C. (I), and also at 50° C. for 48 hours (II), and passing oxygen over the samples initially for 5 seconds. Samples were prepared of mixtures of cinnamic aldehyde and said glycols, cinnamic aldehyde and glycerine and cinnamic aldehyde per se and the following readings were reported:

|  | Tintometer | |
| --- | --- | --- |
|  | Fresh | Aged |
| I | | |
| Cinnamic Aldehyde (CA) | 4 | 11 |
| 50/50 CA + Glycerine | 3; 4 | ~11' |
| 50/50 CA + Propylene Glycol | 3 | 7; 7 = 7 |
| 50/50 CA + Dipropylene Glycol | 3 | 10; 8; 9 = 9 |
| II | | |
| Cinnamic Aldehyde | 4.5 | 7 |
| 50/50 CA/Propylene Glycol | 3.5 | 4.5 |

'Glycerine and CA formed two layers. The glycerine layer (bottom) remained water-white, while the upper layer of CA darkened.

It is noted that the propylene glycol mixture is slightly less dark than the dipropylene glycol mixture, but considerably lighter than the cinnamic aldehyde alone.

It is essential that the pH of the dental cream is either acid or neutral, preferably a pH of about 5-7.5 as shown in Table I. At pH 8.5 or above, the peracid anion forms and epoxidation of cinnamic aldehyde proceeds by Michael addition. This type of addition reaction cannot be intercepted by propylene glycol.

Dental cream yellowing was measured instrumentally on the Colorgard reflectometer. Data reported on the following tables are $+\Delta b$ values (yellow scale) and represent the increase in yellow over unflavored and unaged dental cream which was taken as a zero—b control. Readings taken at 3, 6 and 9 wks at 120° are thought to approximate 1 yr., 2 yrs. and 3 yrs. at room temperature. It is approximated that a $\Delta b$ value of 2 to 3 is the range of marginal acceptability, as a $\Delta b$ of 2 is visually a slight off white, and a $\Delta b$ of 4 is a slight yellow-tan.

TABLE 1

| Cinnamic Aldehyde Discoloration in Dental Cream (Ex. 1) | | | |
| --- | --- | --- | --- |
| | Aging at 120° F.: $\Delta b$- values | | |
| Influence of pH | 3 wks | 6 wks | 9 wks |
| 1% CA pH 5.0 (Citric Acid) | 4.25 | 5.5 | 5.1 |
| 1% CA pH 6.9 to 7.1 (Example 1) | 4.5 | 7.5 | 8.0 |
| 1% CA pH 8.5 (NAHCO$_3$) | 7.5 | 10.5 | 11.2 |

It is also essential that the dentifrice, particularly the aqueous dentifrice, be free of oxidizing agents such as hydrogen peroxide, or salts delivering hydrogen peroxide such as sodium perborate, peracids and salts of peracids. The presence of said oxidizing agents in an aqueous medium would interfere with the preferential reaction of the glycol with the cinnamic aldehyde in the formation of the glycol acetals. As discussed with reference to the necessity of maintaining an acid to neutral pH in the dental vehicle, the presence of the peracid anion proceeds to epoxidation of cinnamic aldehyde by Michael addition.

Experiments with various dental bases showed that discoloration of cinnamic aldehyde in Example 2 was approximately half that of Example 1. Also the discoloration in a bicarbonate base gave a very intense yellow. These differences were identified as being due to pH differences and also to the presence of TiO$_2$ as shown:

|  | pH | TiO$_2$ |
| --- | --- | --- |
| Example 1 | 6.9 to 7.1 | 0 |
| Example 2 | 6.15 | 0.5% |

Lowering the pH of Example 1 through the addition of either citric or phosphoric acid reduced yellowing (Table I).

Increasing pH to 8.5 by adding NaHCO$_3$ significantly increased yellowing.

These observations are consistent with the autoxidation mechanism previously outlined. The peracid anion is formed at a pH 8.5 and epoxidation proceeds more rapidly by Michael Addition. Peracids are substantially weaker than the corresponding carboxylic acid. The pKa of percinnamic acid is estimated to be 7.5. In a neutral base, both free acid and anion would be present. By lowering the pH the reactions due to the anion addition would be prevented.

As noted with the Example 1 vs. Example 2 comparison, the presence of TiO$_2$ provides a reduction of yellowing both visually and instrumentally. Based on a number of comparisons with and without TiO$_2$, a $\Delta b$ reduction of 1.0 is observed with 1% TiO$_2$ and 0.5 with 0.5% TiO$_2$.

An optionally desirable additive which assists in the reduction of cinnamic aldehyde yellowing in dental formulations is titanium dioxide (TiO$_2$) in minor amounts of about 0.5-1% by weight. Table II shows the effectiveness of propylene glycol in reducing yellowing in dental creams containing several cinnamic aldehyde containing flavors in the presence and absence of TiO₂.

TABLE II
Flavor Discoloration in Dental Cream (Example 1)

| | 3 wks | 6 wks | 9 wks |
|---|---|---|---|
| Flavor | | | |
| Cinnamic Aldehyde (CA) | | | |
| 1% CA | 4.5 | 7.5 | 8.0 |
| 1% CA + 35% dipropylene glycol or propylene glycol + 64% Dicalcium Phosphate dihydrate | 0.2 | — | — |
| Spice 10 (S10)' | | | |
| 1% S1O | 3.0 | 4.2 | 4.6 |
| 1% S1O (Glycerine replaced by Propylene Glycol) | 2.3 | 2.7 | — |
| 1% S1O (Glycerine replaced by Propylene Glycol) + 1% TiO₂ | 0.7 | — | — |

'Spice 10 Flavor contains 55% cinnamic aldehyde

Other flavor compositions containing cinnamic aldehyde include:
White Spice-1 which contains 30% cinnamic aldehyde
White Spice-2 which contains 25% cinnamic aldehyde
Spice 11 Flavor which contains 55% cinnamic aldehyde
Spice 12 Flavor which contains 15% cinnamic aldehyde The cinnamic aldehyde flavor compositions may be completed to 100% with flavor components such as menthol, eugenol, peppermint, spearmint, clove, anethole, methylsalicylate, vanillin and the like in various mixtures. Menthol and eugenol are not involved in the yellowing of the dental formulations.

By blending cinnamic aldehyde with propylene glycol or dipropylene glycol, incorporating TiO₂ and reducing pH, high levels of cinnamic aldehyde may be acceptable. This can readily be accomplished by replacing the glycerine or the water with propylene glycol, in the dentifrice formulation.

The flavors containing at least about 5% cinnamic aldehyde in the complete flavor, such as Spice 10 or Spice 12, discolor in white dental cream. If the dental cream is colored green, yellowing is not visually evident.

The dental base utilized in present invention may be in the form of a paste, cream or liquid mouthwash, comprising known ingredients conventionally used in the dentifrice art.

Paste or cream dentifrices may be based on aqueous or substantially anhydrous systems. The former will usually include substantial proportions of finely divided, solid polishing agent, surface active agent, gelling agent, water and some non-aqueous vehicle, e.g., glycerol, sorbitol, and will be opaque; whereas the anhydrous system may be opaque or a clear gel containing a particulate solid polishing agent, surface active agent, gelling agent, and a non-aqueous liquid vehicle comprising propylene glycol or dipropylene glycol solely or admixed with other non-aqueous liquid vehicles such as sorbitol or glycerine, provided said liquid glycol vehicle constitutes at least 10% of the formulation.

The surface active agent, or detergent, present in the dentifrice may sometimes be cationic or amphoteric but will usually be anionic or nonionic. Of these compounds, the anionics are the most preferred. The anionic detergents or surface active agents also usually serve as foaming agents. Among the useful anionic detergents may be mentioned the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl potassium sulfoacetates; higher fatty acid esters of 1,2-dihydroxypropane sulfonates, magnesium salt; the substantially saturated higher aliphatic acyl amides of lower aliphatic aminocarboxylic acid alkali metal salts, such as those having 12 to 16 carbon atoms in the fatty acyl radicals, higher alkyl poly-lower alkoxy (of 10 to 100 alkoxies) sodium alkyl sulfates; higher fatty acid sodium and potassium soaps of coconut oil and tallow, and the like. As noted, most frequently the detergents are sulfated or sulfonated compounds. Examples of useful anionic amides which may be employed are N-lauroyl sarcosine and the sodium, potassium and ethanolamine salts of N-lauroyl-, N-myristoyl- and N-palmitoyl sarcosines. In the above descriptions, "higher" refers to chain lengths of 12 to 22 carbon atoms, preferably of 12 to 18 carbon atoms and most preferably of 12 to 16 carbon atoms. Lower means 2 to 4 carbon atoms, preferably 2 to 3 carbon atoms and most preferably, two carbon atoms.

The nonionic detergents include those containing chains of lower alkylene oxide, e.g., ethylene oxide, propylene oxide, in which there are present from 10 to 100 or more moles of lower alkylene oxide. Among such materials are the block co-polymers of ethylene oxide, propylene oxide and propylene glycol, sold as Pluronics; the alkyl phenyl polyethoxy ethanols, sold as Igepals; mixed co-polymers of ethylene oxide and propylene oxide, sold as Ucons; and various other well known nonionics derived from fatty alcohols or acids and polyethylene oxide. The amphoteric or ampholytic agents and cationics include long chain (alkyl) amidoalkylene-alkalalated amine derivatives, such as "Miranols," e.g., Miranol C₂M; and cationic germicidal detergents, such as diisobutylphenoxyethoxyethyl dimethyl benzyl ammonium chloride; benzyl dimethyl stearyl ammonium chloride; and tertiary amines having a higher fatty alkyl group and two polyoxyethylene groups attached to the nitrogen thereof.

The detergents constitute about 0.5–5% and preferably up to 3% by weight of the dentifrice composition.

Toothpastes, dental creams and toothpowders conventionally contain substantially water insoluble polishing agents or abrasives which are compatible with the formulation, in amounts from about 20–75% by weight of the total cream or paste formulation and up to 95% in toothpowders. Suitable polishing agents include anhydrous dicalcium phosphate, tricalcium phosphate dihydrate, tricalcium phosphate, insoluble sodium metaphosphate, crystalline silica, colloidal silica, complex aluminosilicates, aluminum hydroxide (including alumina trihydrate or hydrated alumina), magnesium phosphate, magnesium carbonate, calcium carbonate, calcium pyrophosphate, bentonite, talc, calcium silicate, calcium aluminate, aluminum oxide, aluminum silicate, and silica xerogels. Most of the polishing agents mentioned are most useful in the preparation of opaque dentifrices but some of them, such as the colloidal silicas, especially the silica xerogels, and complex sodium aluminosilicates, may be utilized in the manufacture of clear dentifrices, because their indexes of refraction approximate those of the rest of the dentifrice constituents in an appropriate vehicle.

In dental cream or toothpaste dentifrice formulations, the liquids and solids should necessarily be proportioned to form a creamy mass of desired consistency which for example is extrudable from a collapsible aluminum tube. In general, the liquids in the dental cream will comprise chiefly water, glycerine, sorbitol, polyethylene glycol, propylene glycol or dipropylene glycol including suitable mixtures thereof. It is advantageous usually to use a mixture of both water, and a humectant such as glycerine, sorbitol, propylene glycol, dipropylene glycol or mixtures thereof. The total liquid content will generally be about 20–75% by weight of the formulation. It is preferred to use also a gelling agent in dental creams such as the natural and synthetic gum-like materials, e.g. Irish Moss, gum tragacanth, sodium carboxymethylcellulose, polyvinylpyrrolidone, or starch. Irish Moss and sodium carboxymethylcellulose, are compatible particularly and are preferred gelling agents. The gum content is usually in an amount up to about 10% and preferably about 0.3–5% by weight of the formulation. Fillers such as pyrogenic silica and silica aerogel may also be used, typically in amounts up to about 10% by weight to supplement the gelling agent. These colloidal silica aerogels which include Syloids 244 and 266 and Aerosil, and the pyrogenic silica sold as Cab-O-Sil may be used as gelling and thickening agents.

The liquid vehicle in the form of a mouthwash usually includes ethyl alcohol, glycerine, sorbitol, propylene glycol, dipropylene glycol, water and mixtures thereof, in an amount of about 90–98% total liquid content by weight.

Various other materials may also be incorporated into the dental vehicle. Examples thereof are fluorine-containing compounds such as stannous fluoride, potassium stannous fluoride ($SnF_2KP$), sodium hexafluorostannate, stannous chlorofluoride, sodium fluorozirconate and sodium monofluorophosphate. These materials, which dissociate or release fluorine-containing ions in water, may be present in the dental vehicle in an effective, but nontoxic amount, usually within the range of about 0.1–5% by weight. Other additives include preservatives such as sodium benzoate, chlorophyll compounds, silicones, ammoniated materials such as urea and diammonium phosphate, phosphates such as tetrasodium pyrophosphate and peroxydiphosphate, antibacterial agents such as benzethonium chloride and other quaternary antibacterial compounds, sweeteners such as sodium saccharin, blue dyes, additional flavors such as peppermint or spearmint and the like. These additives may be used in amounts which do not adversely affect the properties and characteristics of the dentifrice in accordance with present invention. Each constituent may be present in minimal amounts of up to a maximum of 5% by weight and preferably up to 1% by weight of the formulation.

The dentifrice of this invention is prepared by conventional methods of making toothpaste, dental creams, mouthwashes and toothpowder. More specifically, a toothpaste may be prepared by forming a gel with carboxymethylcellulose and water or non-aqueous humectant including propylene glycol or dipropylene glycol, adding thereto with mixing the powdered materials and additional humectant (if desired) followed by the addition with mixing of polishing agent and then the surfactant and the flavor, and tubing the final mixture. The flavor composition may be blended with the propylene glycol or dipropylene glycol color stabilizer prior to addition to the mixture.

In the practice of this invention to promote oral hygiene, the dentifrice according to this invention is applied regularly to dental enamel by brushing the teeth for 30–90 seconds at least once daily and/or rinsing the teeth with a mouthwash once daily.

DETAILED DESCRIPTION OF THE INVENTION

The following examples are further illustrative of the nature of the present invention, but it is understood that the invention is not limited thereto. The compositions are prepared in the usual manner and all amounts and proportions referred to herein and in the appended claims are by weight unless otherwise indicated. The flavor ingredient is a cinnamic aldehyde or citral-containing flavorant composition to which propylene glycol or dipropylene glycol is added as described in the experiments following the examples (Table III).

EXAMPLE 1

| Dental Cream | |
|---|---|
| Ingredients | % |
| Glycerine | 22.0 |
| Sodium Monofluorophosphate | 0.8 |
| Sodium Carboxymethylcellulose | 1.0 |
| Tetrasodium Pyrophosphate | 0.2 |
| Sodium Saccharin | 0.2 |
| Sodium Benzoate | 0.5 |
| Deionized Water | 24.5 |
| Dicalcium Phosphate Dihydrate | 48.8 |
| Flavor | 0.8 |
| Sodium Lauryl Sulfate | 1.2 |
| pH 6.9–7.1 | |

EXAMPLE 2

| Dental Cream | |
|---|---|
| Ingredients | % |
| Glycerine | 10.0 |
| Sodium Monoflurophosphate | 0.8 |
| Sodium Carboxymethylcellulose | 1.1 |
| Sodium Benzoate | 0.5 |
| Sodium Saccharin | 0.2 |
| Sorbitol (70% Solution) | 17.0 |
| Deionized Water | 22.2 |
| Titanium Dioxide | 0.4 |
| Insol. Sodium Metaphosphate | 39.3 |
| Hydrated Alumina | 1.0 |
| Anhy. Dicalcium Phosphate | 5.0 |
| Flavor | 1.0 |
| Sodium Lauryl Sulfate | 1.5 |
| pH 6.15 | |

EXAMPLE 3

| Non-Aqueous Dental Cream | |
|---|---|
| Ingredients | % |
| Propylene Glycol | 43.4 |
| Klucel GF' (Hercules) | 1.5 |
| Sodium Saccharin | 0.2 |
| $TiO_2$ | 0.4 |
| Dicalcium Phosphate Dihydrate | 50.0 |
| Peroxydiphosphate | 3.0 |
| Sodium Lauryl Sulfate | 1.5 |

-continued

Non-Aqueous Dental Cream

| Ingredients | % |
|---|---|
| pH 6.4 | |

'Hydroxypropyl cellulose - a propylene glycol ether of cellulose

EXAMPLE 4

Aqueous Dental Cream

| Ingredients | % |
|---|---|
| Propylene Glycol | 22.0 |
| Sodium Monofluorophosphate | 0.8 |
| Sodium Carboxymethylcellulose | 1.0 |
| Tetrasodium Pyrophosphate | 0.2 |
| Sodium Saccharin | 0.2 |
| Sodium Benzoate | 0.5 |
| Dicalcium Phosphate Dihydrate | 48.8 |
| Spice 10 | 0.9 |
| Sodium Lauryl Sulfate | 1.2 |
| TiO$_2$ | 1.0 |
| H$_2$O | Q.S. |

EXAMPLE 5

Mouthwash

| Ingredients | % |
|---|---|
| Ethyl alcohol | 15–30 |
| Propylene Glycol | 10–15 |
| Polysorbate 80[1] | 2–3 |
| Poloxamer 338[2] | 0–0.5 |
| Benzethonium chloride | 0–0.075 |
| Flavor composition | 0.1–0.5 |
| Deionized Water | Balance |

[1] A mixture of oleate esters of sorbitol and sorbitol anhydrides, consisting of the monoester condensed with approximately 20 moles of ethylene oxide.
[2] The polyoxyethylene polyoxypropylene block polymer that conforms to the formula: insert ring
wherein x and z = 128, and y = 54

Flavor levels in mouthwash are generally less than in a dental cream.

EXAMPLE 6

Dental Powder

| Ingredients | % |
|---|---|
| Magnesium Silicate | 7.0 |
| Sodium Saccharin | 0.2 |
| Flavor | 2.5 |
| Dicalcium Phosphate-Anhy. | 88.3 |
| Sodium Lauryl Sulfate | 2.0 |

Flavor levels in dental powders are generally greater than in dental creams.

The following table represents discoloration results upon aging at 120° F. of the dental cream of Example 1 unless otherwise specified, both unflavored and containing cinnamic aldehyde (CA) flavorant per se and with propylene glycol or dipropylene glycol to prevent or reduce the discoloration caused by the cinnamic aldehyde ingredient.

The b values in the table represents the dental cream yellowing measured on the Colorgard reflectometer and the Δb value represents the increase in yellowing from the unaged and unflavored sample which is the zero b control.

TABLE III

Dental Cream Discoloration Studies
120° F., Aging in Dental Cream of Example 1

| | 1 wk | | 3 wks | | 6 wks | |
|---|---|---|---|---|---|---|
| | b | Δb | b | Δb | b | Δb |
| Experiment I | | | | | | |
| 1% CA in Ex. 3 | 2.3 | + 0.3 | 3.8 | + 1.8 | 5.1 | + 3.4 |
| 1% CA + 1% Limonene in Ex. 3 | 1.7 | + 0 | 3.3 | + 1.3 | 4.6 | + 2.9 |
| 1% CA + 10% Propylene Glycol | 4.0 | + 1.8 | 5.0 | + 3.0 | 7.1 | + 5.4 |
| 1% CA + 36% Propylene Glycol + 63% Dical phosphate | 2.0 | + 0 | 1.8 | + 0 | Sample solidified | |
| Experiment II | | | | | | |
| 1% CA | 5.1 | + 3.2 | 12.6 + 10.4 | | 10.4 | + 6.7 |
| 1% CA + 1% Propylene Glycol | 5.2 | + 3.3 | 9.6 | + 7.4 | 8.0 | + 4.3 |
| 1% CA + 1% Dipropylene Glycol | 4.5 | + 2.6 | 8.6 | + 6.4 | 6.4 | + 2.7 |
| 1% CA + 5% Propylene Glycol | 4.9 | + 3.0 | 8.3 9.1 + 6.5 | | 6.6 | + 2.9 |
| 1% CA + 5% Dipropylene Glycol | 4.4 | + 2.5 | 8.0 | + 5.8 | 5.0 | + 1.3 |
| 1% CA + 35% Dipropylene Glycol + 64% Dical Phosphate | 1.8 | + 0 | 2.4 | + 0.2 | 2.9 | + 0 |
| Experiment III | | | | | | |
| 1% Spice 10 | 3.9 | + 2.1 | 5.7 | + 3.6 | 5.7 | + 3.9 |
| | 3.9 | + 2.1 | 5.8 | + 3.7 | 5.6 | + 3.8 |
| 1% Spice 10 + 5% Propylene Glycol | 3.7 | + 1.9 | 5.5 | + 3.4 | 5.8 | + 4.0 |
| 1% Spice 10 + 5% Propylene Glycol + 1% Limonene | 3.9 | + 2.1 | 5.8 | + 3.7 | 5.9 | + 4.1 |
| 1% Spice 10 + 5% Propylene Glycol + 1% TiO$_2$; pH 5.1 | 2.4 2.7 | + 0.6 + 0.9 | 3.9 3.7 | + 1.8 + 1.6 | — | |
| Experiment IV | | | | | | |
| 0.9% Spice 10 | 3.9 | + 1.7 | 6.4 | + 4.0 | 6.5 | + 4.7 |
| 0.9% Spice 10 in Ex. 4 | 3.3 | + 1.1 | 4.7 | + 2.3 | 4.5 | + 2.7 |
| Experiment V | | | | | | |
| 0.9% Spice 10 in Ex. 4 + 1% TiO$_2$ | 2.8 | + 0.7 | 2.7 | − 0 | — | |

Table III discloses formulations containing a variety of flavorants containing cinnamic aldehyde which yellow upon aging, and the reduction of said yellowing by the addition of propylene glycol and dipropylene glycol, or by the use of said glycols as the sole humectat i.e. Examples 3 and 4, in large amounts. The adjustment of the pH to about 6 and the addition of TiO$_2$ further reduce the yellowing of these flavor-containing formulations.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

We claim:

1. A white dentifrice formulation having improved stability against yellowing discoloration upon aging, comprising about 0.1–1% by weight of an unsaturated aldehyde-containing flavorant selected from the group consisting of cinnamic aldehyde and citral, which is subject to discoloration with aging, and an effective amount in excess of 5% by weight of propylene glycol or dipropylene glycol to impart color stability against aging, in a dental vehicle free of oxidizing agents and having a slightly acid to alkaline pH below 8.5.

2. The dentifrice, according to claim 1, wherein the discoloration inhibitor constitutes about 10–45% by weight of the formulation.

3. The dentifrice according to claim 2 wherein the dental vehicle is an anhydrous dental cream.

4. A dentifrice according to claim 2 wherein the dental vehicle is an aqueous dental cream.

5. The dentifrice according to claim 2, wherein the dentifrice has a pH of about 5 to 7.5.

6. The dentifrice according to claim 5, wherein the dentifrice is a white color stabilized dental cream, containing about 20–70% by weight of a water insoluble polishing agent.

7. The dentifrice according to claim 6, which additionally contains about 0.5–1% by weight of titanium dioxide.

8. The dentifrice according to claim 5, wherein the dentifrice is a white color stabilized mouthwash, containing a liquid content of about 90–98% by weight.

9. The dental cream according to claim 6 containing 1% cinnamic aldehyde flavor and 22% propylene glycol as discoloration inhibitor.

10. The dental cream according to claim 6 containing 1% cinnamic aldehyde flavor and 35% dipropylene glycol as discoloration inhibitor.

11. The anhydrous dental cream according to claim 3 containing 1% cinnamic aldehyde flavor and 43% propylene glycol.

12. The anhydrous dental cream according to claim 3, containing 1% cinnamic aldehyde flavor and 22% propylene glycol and 1% titanium dioxide.

13. The mouthwash according to claim 8, which is anhydrous, and contains 10–15% propylene glycol and 0.1–0.5% cinnamic aldehyde.

14. The mouthwash according to claim 8 containing 0.1–0.5% by weight of a flavor composition containing cinnamic aldehyde or citral.

15. A dental cream according to claim 7 containing 0.1–1% by weight of a flavor composition containing cinnamic aldehyde or citral.

16. A dentifrice according to claim 1 containing about 0.05–5% surfactant.

17. A dentifrice according to claim 1, in the form of a dental cream containing a liquid content of about 20–75% by weight of the composition.

* * * * *